(12) United States Patent
Sugimoto et al.

(10) Patent No.: US 8,896,822 B2
(45) Date of Patent: Nov. 25, 2014

(54) METHOD OF MEASURING CUT-OFF WAVELENGTH OF OPTICAL FIBER

(75) Inventors: Yasuko Sugimoto, Sakura (JP); Shoichiro Matsuo, Sakura (JP)

(73) Assignee: Fujikura Ltd., Tokyo (JP)

( * ) Notice: Subject to any disclaimer, the term of this patent is extended or adjusted under 35 U.S.C. 154(b) by 70 days.

(21) Appl. No.: 13/440,757

(22) Filed: Apr. 5, 2012

(65) Prior Publication Data

US 2012/0262706 A1 Oct. 18, 2012

(30) Foreign Application Priority Data

Apr. 7, 2011 (JP) ................................. 2011-085520

(51) Int. Cl.
*G01N 21/00* (2006.01)
*G01N 21/84* (2006.01)
*G02B 6/02* (2006.01)

(52) U.S. Cl.
CPC . *G01N 21/84* (2013.01); *G02B 6/02* (2013.01)
USPC ......................................................... 356/73.1

(58) Field of Classification Search
USPC ............................................. 356/73.1; 372/6
See application file for complete search history.

(56) References Cited

U.S. PATENT DOCUMENTS

| 4,636,070 A | * | 1/1987 | Ide ................................ 356/73.1 |
| 2009/0129409 A1 | * | 5/2009 | Hirano et al. ...................... 372/6 |

FOREIGN PATENT DOCUMENTS

| JP | 2005-003794 A | 1/2005 |
| JP | 2010-139381 A | 6/2010 |
| JP | 2010-237185 A | 10/2010 |

OTHER PUBLICATIONS

Nakanishi, T.; Hirano, Masaaki; Sasaki, T., "Proposal of reliable cutoff wavelength measurement for bend insensitive fiber," Optical Communication, 2009. ECOC '09. 35th European Conference on , vol., No., pp. 1,2, Sep. 20-24, 2009.*

Nakanishi, Tetsuya, et al., "Proposal of Reliable Cutoff Wavelength Measurement for Bend Insensitive Fiber," 2009 The Institute of Electronics, Information and Communication Engineers Communications Society Conference, B-10-10, pp. 190.

Japanese Office Action for corresponding Application No. 2011-085520 issued Jul. 1, 2014.

* cited by examiner

*Primary Examiner* — Tarifur Chowdhury
*Assistant Examiner* — Jamil Ahmed
(74) *Attorney, Agent, or Firm* — Sughrue Mion, PLLC

(57) ABSTRACT

A cut-off wavelength measuring method according to the present invention includes: preparing a single mode fiber as a reference fiber; preparing a measurement target fiber; adjusting the length of the single mode fiber such that the length of the single mode fiber is longer than the that of the measurement target fiber at the time of measuring power of transmission light and the reference fiber propagates only light of a base mode at a predicted cut-off wavelength of the measurement target fiber; measuring wavelength dependence of power of light transmitted through the reference fiber and wavelength dependence of power of light transmitted through the measurement target fiber; and calculating a cut-off wavelength of the measurement target fiber based on wavelength dependence represented as the ratio of the power of transmission light transmitted through the measurement target fiber to the power of light transmitted through the reference fiber.

5 Claims, 8 Drawing Sheets

METHOD OF MEASURING CUT-OFF WAVELENGTH OF OPTICAL FIBER

CROSS-REFERENCE TO RELATED APPLICATION

This application is based on and claims priority from Japanese Patent Application No. 2011-085520, filed on Apr. 7, 2011, the contents of which are incorporated herein by reference.

BACKGROUND OF THE INVENTION

1. Field of the Invention

The present invention relates to a silica-based optical fiber that is used for optical fiber communication, and more particularly, to a method of measuring a minimum wavelength of a single-mode fiber for which the propagation mode is single, that is, a cut-off wavelength in the fiber.

2. Background Art

As a conventional method of measuring the cut-off wavelength of a single mode fiber, particularly, as a method of measuring an effective cut-off wavelength, for example, as illustrated in "Opto-electronic Measuring Instruments Guide, Thoroughly-Revised Edition", Optronics Co., Ltd., Published on Jun. 24, 2004, a bending method and a multi-mode excitation method are known.

In the bending method, a cut-off wavelength is calculated by using the difference between loss properties measured in a state in which a bending portion is not added to a single-mode fiber and a state in which a bending portion is added to the single mode fiber.

Schematic configurations of measurement systems for measuring a fiber cut-off wavelength according to the bending method by using a strand having a length of 2 m are illustrated in FIGS. 11A and 11B.

FIG. 11A illustrates a case where a bending portion is not effectively added to a measurement target fiber.

FIG. 11B illustrates a case where a bending portion is effectively added to the measurement target fiber.

In FIGS. 11A and 11B, reference numeral 10 is a light source unit.

The light source unit 10, for example, is configured of a white light source and a spectroscope that spectrally disperses white light emitted from the white light source.

The light emitted from the light source unit 10 is guided by a measurement target fiber 12 so as to be received by a light receiving unit 14.

As the measurement target fiber 12, the same single mode fiber is used in the case where a bending portion is added thereto (FIG. 11B) and a case where a bending portion is not added thereto (FIG. 11A).

In a case where measurement is performed without a bending portion being added to the measurement target fiber 12 (FIG. 11A), transmitted light is received by the light receiving unit 14 in a state in which a bending portion is not effectively added to the measurement target fiber 12.

On the other hand, in a case where measurement is performed with a bending portion being added to the measurement target fiber 12 (FIG. 11B), transmitted light is received by the light receiving unit 14 in a state in which a small bending portion B1 (for example, a bending portion of 60 mmφ is added to the measurement target fiber 12.

In the states illustrated in FIGS. 11A and 11B, the wavelength dependence of the transmission light power is measured.

A cut-off wavelength is calculated based on the ratio between the transmission light power in a case where there is bending and the transmission light power in a case where there is no bending.

Accordingly, the above-described bending method may be called a measurement method using a difference in bending loss between a base mode and a higher order mode of a single mode fiber.

In the cases illustrated in FIGS. 11A and 11B, a bending portion B2 of 280 mmφ is disposed on the measurement target fiber 12.

This is a bending portion that is determined based on standards.

The bending portion of 280 mmφ is a bending portion that does not substantially cause any bending loss.

In the description presented here, the "standards" represent standards on the measurement of a cut-off wavelength such as IEC 60793-1-44 "Measurement methods and test procedures—Cut-off wavelength", ITU-T G. 650.1 "Definitions and test methods for linear, deterministic attributes of single-mode fibre and cable", and JIS C 6825 "Test methods for structural parameters of optical fibers—Optical characteristics".

On the other hand, the multi-mode excitation method is a method of measuring a cut-off wavelength based on the ratio between the power of transmitted light transmitted through a multi-mode fiber (reference fiber) used as a reference, for example, a multi-mode fiber having a short length of 1 to 2 m and the transmission light power in a case where the measurement target fiber is excited in a multi-mode.

Schematic configurations of measurement systems used when a cut-off wavelength is measured by using the multi-mode excitation method are illustrated in FIGS. 12A and 12B.

FIG. 12A illustrates a measurement method using a reference fiber.

As the reference fiber 16, a multi-mode fiber having a short length is used, and the transmission light power of the reference fiber 16 is measured.

On the other hand, FIG. 12B illustrates a measurement method using a measurement target fiber.

Here, a reference fiber 16 is prepared which is configured of the same multi-mode fiber as the fiber used in the reference measurement.

The measurement target fiber 12 is connected to the output end of the reference fiber 16, and light transmitted through the reference fiber 16 and the measurement target fiber 12 is received by the light receiving unit 14 so as to measure the power of the transmitted light.

The cut-off wavelength of the measurement target fiber 12 is calculated based on the wavelength dependence that is represented by the ratio between the power of transmission light transmitted through the reference fiber 16 and the power of transmission light transmitted through the reference fiber 16 and the measurement target fiber 12.

This multi-mode excitation method is a method using a phenomenon in which the power of transmission light transmitted through the measurement target fiber 12 markedly changes in a wavelength region in which the mode is switched from a multi-mode to a single mode.

For measuring the measurement target fiber using the multi-mode excitation method (FIG. 12B), two bending portions (B3 and B4) of 80 mmφ formed so as to make one complete rotation around the measurement target fiber 12 are disposed at both ends of the measurement target fiber.

The reason for disposing the bending portions is that it is defined in the standard that one circulation of a bending portion of 80 mmφ and a plurality of circulations of a bending portion of 280 mmφ are arranged at both ends of a sample in a case where the cable cut-off wavelength is measured by using the sample having a length of 22 m.

In addition, in a case where the cut-off wavelength of a fiber using a strand of 2 m as the length of the measurement target fiber 12 is measured, similarly to the above-described bending method, the bending portions B3 and B4 are not disposed.

As cut-off wavelengths defined in the standards, there are a cable cut-off wavelength measured by using a fiber cable having a length of 22 m, a cable cut-off wavelength measured by using a fiber strand having a length of 22 m, a fiber cut-off wavelength measured by using a fiber strand having a length of 2 m, and a jumper cable cut-off wavelength measured by using a jumper cable having a length of 2 m.

In the methods of measuring the cut-off wavelength, while the methods of measuring the measurement target fiber are different from each other, as the method of measuring the reference fiber, one of the bending method and the multi-mode excitation method is used.

Incidentally, recently, low-bending loss optical fibers such as an HAF (Hole Assisted Fiber) and a trench-type optical fiber have been actively developed.

The low-bending loss optical fibers of such a kind are designed such that the effect of confining light in the core is increased.

In such low-bending loss optical fibers, the confinement effect is also increased for a higher order mode, and accordingly, it is difficult to remove the higher order mode with the degree of bending that is applied in the bending method.

Accordingly, it is difficult to calculate the cut-off wavelength with accuracy in the bending method.

Therefore, conventionally, in order to measure the cut-off wavelength of the low-bending loss optical fiber of such a kind, the multi-mode excitation method is generally used.

Now, the method of measuring the cut-off wavelength according to the multi-mode excitation method will be described in detail with reference to FIG. 13.

First, as described above, the power $P_{sig}(\lambda)$ of transmission light transmitted through a measurement target fiber and the power $P_{ref}(\lambda)$ of transmission light transmitted through a multi-mode fiber used as a reference fiber are measured, and the ratio $A(\lambda)$ of the transmission light power $P_{sig}(\lambda)$ to the transmission light power $P_{ref}(\lambda)$ is acquired as a logarithmic ratio using $A(\lambda)=10\times\log_{10}\{P_{sig}(\lambda)/P_{ref}(\lambda)\}$.

The wavelength dependence spectrum of the ratio $A(\lambda)$ is denoted by a thick solid line 18 in FIG. 13.

Here, in the measurement target fiber, from a long wavelength side toward a short wavelength side, the power $P_{sig}(\lambda)$ of the transmission light transmitted through the measurement target fiber drastically increases at a position close to a wavelength changing from the single mode propagation region (a region in which only light of the base mode is propagated) to the multi-mode propagation region (a region in which not only light of the base mode but also light of the higher order mode is propagated).

Accordingly, the wavelength dependence of the ratio $A(\lambda)$ of the power $P_{sig}(\lambda)$ of transmission light transmitted through the measurement target fiber to the power $P_{ref}(\lambda)$ of transmission light transmitted through the multi-mode fiber used as a reference fiber, as illustrated in FIG. 13, also drastically increases from the long wavelength side to the short wavelength side at a position close to the wavelength for which the measurement target fiber changes from the single mode propagation region 20 to the multi-mode propagation region 22.

Thus, a straight line that is acquired by linearly approximating the spectrum, which is positioned on the long wavelength side corresponding to the single mode propagation region, of the measurement target fiber in compliance with a standard such as JIS will be referred to as a reference line (a thin solid line 24 shown in FIG. 13).

In addition, a wavelength corresponding to an intersection 28 of a straight line (a dashed-two dotted line 26 shown in FIG. 13) acquired by shifting the reference line by 0.1 dB in a parallel manner and the spectrum of the transmission light power ratio $A(\lambda)$ is defined as a cut-off wavelength $\lambda$.

However, in the cut-off wavelength measurement according to the multi-mode excitation method, there are the following problems.

Since multi-mode propagation is performed by using the multi-mode fiber as the reference fiber, a variation (a variation in the shape of a wave shape, a ripple shape, or a hump shape) occurs over the entire multi-mode propagation wavelength region in the power $P_{ref}(\lambda)$ of the transmission light due to the wavelength dependence of the loss property.

For the power $P_{sig}(\lambda)$ of the transmission light transmitted through the single mode fiber used as the measurement target fiber, in a region (in other words, the single mode propagation region in which only light of the base mode is propagated) 20 located on the long wavelength side of the cut-off wavelength, single mode propagation is performed.

Accordingly, a large variation in the wave or the like does not substantially occur.

In addition, also in the transmission light power ratio $A(\lambda)$, due to the wave occurring in the wavelength dependence of the loss property of the reference fiber, as illustrated in FIG. 13, a variation called a wave, a ripple, a hump (bump), or the like (hereinafter, it will be referred to as a "wave" as being a representative thereof) occurs in the wavelength property of the single mode propagation region 20 of the measurement target fiber.

Accordingly, in a case where the reference line 24 is determined by linearly approximating the long wavelength side of the transmission light power ratio $A(\lambda)$, the cut-off wavelength $\lambda$ acquired from an intersection 28 of the straight line 26 acquired by shifting the reference line 24 by 0.1 dB and the transmission light power ratio $A(\lambda)$ on the short wavelength side without avoiding the occurrence of incorrectness, and cannot necessarily be considered as having an accurate value.

In other words, according to the linear approximation technique for a case where the reference line 24 is determined, deviation of different values of cut-off wavelengths from the same measurement data of the ratio of the power of the transmission light cannot be avoided, in other words, a variation occurs in the calculated cut-off wavelength depending on the calculation method.

Here, although the policy of the linear approximation technique for determining the reference line 24 is represented in the standards, a precise processing method for the wave or the like has not been determined.

As a method of measuring the cut-off wavelength that can solve the above-described problems of the multi-mode excitation method, a method called a single mode fiber reference method has been proposed in "2009 Processing 2 of the Society Conference of the Institute of Electronics, Information and Communication Engineers, Page 190, Proposal of Reliable Cut off Wavelength Measurement for Bend Insensitive Fiber".

According to the single mode fiber reference method, instead of the multi-mode fiber used in the multi-mode excitation method, a single mode fiber having a wavelength shorter than that of the measurement target fiber is prepared as the reference fiber.

Then, the power $P_{sig}(\lambda)$ of the transmission light transmitted through the measurement target fiber and the power $P_{ref}(\lambda)$ of the transmission light in a state in which a small bending portion of 60 mmϕ is added to a single mode fiber (a fiber having a cut-off wavelength shorter than that of the measurement target fiber) used as the reference fiber are measured.

The ratio $A(\lambda)$ of the transmission light power $P_{sig}(\lambda)$ to the transmission light power $P_{ref}(\lambda)$ is acquired by using the same method as that described above, and a long wavelength-side portion of the spectrum of the transmission light power ratio $A(\lambda)$ is linearly approximated so as to acquire a reference line.

In addition, a wavelength corresponding to the short wavelength-side intersection of a straight line acquired by shifting the reference line by 0.1 dB and the transmission light power ratio $A(\lambda)$ is determined as a cut-off wavelength.

In the single mode fiber reference method, a single mode fiber having a cut-off wavelength shorter than that of the measurement target fiber, to which a small bending portion of 60 mmϕ is added, is used as the reference fiber.

Accordingly, unlike the case of the multi-mode excitation method, at least a large fluctuation does not occur in the transmission light power ratio $A(\lambda)$ at least on the side of the long wavelength (single mode propagation region) longer than that at a position close to the cut-off wavelength of the measurement target fiber.

Accordingly, the reference line can be uniquely determined in an easy manner, and, as a result, the cut-off wavelength can be uniquely determined in an easy manner, whereby the occurrence of a variation in the calculated cut-off wavelength can be avoided.

Thus, in the single mode fiber reference method proposed in "2009 Processing 2 of the Society Conference of the Institute of Electronics, Information and Communication Engineers, Page 190, Proposal of Reliable Cut off Wavelength Measurement for Bend Insensitive Fiber", there are the following problems.

In the single mode fiber reference method, in order to perform accurate measurement, it is necessary to use a fiber having a cut-off wavelength that is sufficiently shorter than that of the measurement target fiber as a single mode fiber of the reference fiber.

In other words, in a case where a single mode fiber having a cut-off wavelength that is slightly shorter than that of the measurement target fiber is used as the reference fiber, between wavelength dependence of the power of transmission light transmitted through the measurement target fiber and that of the transmission light transmitted through the reference fiber, the transmission light power ratio $A(\lambda)$ that is sufficient for calculating a cut-off wavelength cannot be acquired.

Accordingly, there is a case where it is difficult to accurately calculate a cut-off wavelength.

Accordingly, in the proposal disclosed in "2009 Processing 2 of the Society Conference of the Institute of Electronics, Information and Communication Engineers, Page 190, Proposal of Reliable Cut off Wavelength Measurement for Bend Insensitive Fiber", such problems are not considered, and, accordingly, there is concerned that accurate measurement cannot be performed.

Furthermore, in a case where the cut-off wavelength of a measurement target fiber is to be newly measured, there are cases where the cut-off wavelength of the measurement target fiber is shorter than the cut-off wavelengths of all the single mode fibers, which are known, prepared in advance.

In such a case, a reference fiber cannot be selected from the single mode fibers prepared in advance.

Consequently, in a practical measurement site, it cannot be determined that an appropriate reference fiber can be easily prepared in the single mode fiber reference method.

SUMMARY OF THE INVENTION

The present invention is devised in consideration of the above-described situations and is based on the single mode fiber reference method proposed in "2009 Processing 2 of the Society Conference of the Institute of Electronics, Information and Communication Engineers, Page 190, Proposal of Reliable Cut off Wavelength Measurement for Bend Insensitive Fiber". An object of the present invention is to provide a method of measuring a cut-off wavelength that can solve such problems. The inventors of the present invention and others have noticed that the cut-off wavelength of the single mode fiber, which is acquired through measurement, changes in accordance with the length of a fiber used in the measurement of the cut-off wavelength, in other words, the cut-off wavelength is shortened as the length of the fiber is increased.

This point will be described next with reference to FIG. 1.

FIG. 1 is a graph that schematically illustrates the wavelength dependency of the ratio $A(\lambda)$ in a case where the ratio $A(\lambda)$ of the power of transmission light transmitted through a measurement target fiber to the power of transmission light transmitted through a reference fiber is measured according to the multi-mode excitation method by using a general single mode fiber used for communication as the measurement target fiber. A solid line 18A shown in FIG. 1 illustrates the wavelength dependency of the ratio $A(\lambda)$ calculated based on the power of transmission light in a case where a single mode fiber having a short length is the measurement target fiber.

A broken line 18B shown in FIG. 1 illustrates the wavelength dependency of the ratio $A(\lambda)$ calculated based on the power of transmission light in a case where a single mode fiber having a long length is the measurement target fiber.

Here, portions at which $A(\lambda)$ rises steeply from the long wavelength side toward the short wavelength side correspond to cut-off wavelengths λ-A and λ-B.

It is understood that the cut-off wavelength is shortened as the length of the fiber is increased.

From this point of view, in order to measure a cut-off wavelength according to the single mode fiber reference mode by using a reference fiber configured of a single mode fiber, it is understood that a fiber having a cut-off wavelength sufficiently shorter than that of the measurement target fiber can be selected as the reference fiber by selecting a single mode fiber having a length that is sufficiently longer than that of the measurement target fiber as the reference fiber.

Relating to a cut-off wavelength measured from the measurement target fiber, in a step before the measurement of the cut-off wavelength, the relationship between the length of the fiber and the cut-off wavelength can be predicted to some degree based on a calculation using a refractive index profile that is acquired through the measurement of the measurement target fiber or the measurement of a base material used before the drawing of the measurement target fiber.

Thus, it is considered that the cut-off wavelength of the measurement target fiber can be calculated using the following method.

More specifically, first, a predicted value for the length of the fiber to be measured is set as a predicted cut-off wavelength of the measurement target fiber.

The length of the reference fiber is selected such that the reference fiber propagates only light of the base mode for the predicted cut-off wavelength of the measurement target fiber.

It is understood that, by selecting the length of the fiber as above, the cut-off wavelength of the measurement target fiber can be calculated based on a change in the transmission light power ratio $A(\lambda)$ of the power of transmission light transmitted through the measurement target fiber to the power of transmission light transmitted through the reference fiber.

However, in selecting the reference fiber, in a case where the length of the reference fiber is the same as that of the measurement target fiber, and a fiber having a short cut-off wavelength is selected from fibers other than the measurement target fiber in consideration of only the cut-off wavelength of the reference fiber, when there is a variation in the cut-off wavelength on the short wavelength side, a steep change in the ratio $A(\lambda)$ of the power of transmission light transmitted through the measurement target fiber and the power of transmission light transmitted through the reference fiber is not acquired at a position close to the predicted cut-off wavelength of the measurement target fiber, and an accurate cut-off wavelength cannot be calculated.

In contrast to this, by preparing a reference fiber of which the length is adjusted and a measurement target fiber from the same strand in consideration of the relationship between the fiber length and the cut-off wavelength, the ratio $A(\lambda)$ of the power of transmission light transmitted through the measurement target fiber and the power of transmission light transmitted through the reference fiber can be clearly acquired. As a result, it is possible to measure an accurate cut-off wavelength.

In addition, in consideration of the relationship between the length of the fiber and the cut-off wavelength, which is acquired through the above-described calculation, a strand can be prepared which is the same type as that of the measurement target fiber but is different from the measurement target fiber.

Furthermore, in such a case, since an appropriate fiber can be acquired as the reference fiber through the adjustment of the length of the fiber, the degree of freedom for selecting the reference fiber increases, which has been found to be advantageous in a practical measurement site, leading to the present invention.

More specifically, a method of measuring a cut-off wavelength according to a basic aspect (first aspect) of the present invention includes: preparing a single mode fiber as a reference fiber; preparing a measurement target fiber; adjusting the length of the single mode fiber such that the length of the single mode fiber is longer than the length of the measurement target fiber at the time of measuring power of transmission light and the reference fiber propagates only light of a base mode at a predicted cut-off wavelength of the measurement target fiber; measuring wavelength dependence of power of transmission light transmitted through the reference fiber and wavelength dependence of power of transmission light transmitted through the measurement target fiber; and calculating a cut-off wavelength of the measurement target fiber based on wavelength dependence that is represented as a ratio of the power of transmission light transmitted through the measurement target fiber to the power of transmission light transmitted through the reference fiber.

According to such a method of measuring a cut-off wavelength, a single mode fiber is used as a reference fiber.

Accordingly, unlike the multi-mode excitation method, the occurrence of a deviation in the calculated cut-off wavelength due to inaccuracy, which is acquired when a reference line used for calculating the cut-off wavelength is determined, caused by a wave occurring on the long wavelength side of the wavelength dependence of the transmission light power ratio is avoided.

In addition, in such a method of measuring a cut-off wavelength, the length of the single mode fiber is adjusted as described above when the power of transmission light transmitted through the single mode fiber used as the reference fiber is measured.

Accordingly, at a position close to the predicted cut-off wavelength of the measurement target fiber, a clear difference is acquired between the power of transmission light transmitted through the measurement target fiber and the power of transmission light transmitted through the reference fiber.

In addition, by acquiring a steep change in the transmission light ratio $A(\lambda)$, an accurate cut-off wavelength can be measured.

Furthermore, by adjusting the length of the fiber, the cut-off wavelength of the reference fiber is configured to be shorter than the predicted cut-off wavelength of the measurement target fiber.

Accordingly, as the cut-off wavelength of the fiber used as the reference fiber, the cut-off wavelength of the fiber having a length of 2 m or the cut-off wavelength of the fiber having a length of 22 m, which is defined in the standard, does not need to be shorter than the cut-off wavelength of the measurement target fiber.

In addition, a reference fiber that is configured such that the cut-off wavelength of the fiber having a length of 2 m or the cut-off wavelength of the fiber having a length of 22 m is equal to the cut-off wavelength of the measurement target fiber can be appropriately used.

Furthermore, a reference fiber that is configured such that the cut-off wavelength of the fiber having a length of 2 m or the cut-off wavelength of the fiber having a length of 22 m is longer than the cut-off wavelength of the measurement target fiber can also be appropriately used.

Accordingly, the degree of freedom for selecting a reference fiber is markedly higher than that of a conventional method in which a reference fiber is selected in consideration of only the cut-off wavelength.

Therefore, in a practical site at which the cut-off wavelength is measured, fibers prepared in advance are appropriately used as the reference fiber, and the cut-off wavelength can be measured in an easy manner.

According to a method of measuring a cut-off wavelength of a second aspect of the present invention, in the above-described method of measuring a cut-off wavelength according to the first aspect, it is preferable that the length of the single mode fiber used as the reference fiber at the time of measuring the power of the transmission light be adjusted such that the cut-off wavelength of the reference fiber is shorter than the predicted cut-off wavelength of the measurement target fiber by at least 10 nm.

Accordingly to such a method of measuring a cut-off wavelength as the second aspect, the length of the single mode fiber used as the reference fiber is adjusted in consideration of the relationship between the cut-off wavelength that is calculated in advance based on the refractive index profile of the fiber and the length of the fiber.

More specifically, the length of the single mode fiber is adjusted at the time of measuring the power of transmission light such that the cut-off wavelength of the single mode fiber used as the reference fiber is shorter than the predicted cut-off wavelength of the measurement target fiber by at least 10 nm.

Accordingly, a clearer difference between the power of transmission light transmitted through the measurement target fiber and the power of transmission light transmitted through the reference fiber can be obtained at a position close to the predicted cut-off wavelength of the measurement target fiber, and accordingly, a cut-off wavelength can be calculated more accurately.

However, the difference between the cut-off wavelength of the reference fiber and the cut-off wavelength of the measurement target fiber may be a width equal to or larger than 70 nm due to the slope of a steep inclination that can be checked when the wavelength dependence represented as the ratio of the power of transmission light transmitted through the measurement target fiber to the power of transmission light transmitted through the reference fiber, which are actually measured, is represented as a graph.

Since such a difference occurs due to the refractive index profile of the fiber, it can be estimated by acquiring the relationship between the cut-off wavelength of the measurement target fiber and the length of the measurement target fiber based on the refractive index profile of the measurement target fiber.

According to a method of measuring a cut-off wavelength of a third aspect of the present invention, in the above-described method of measuring a cut-off wavelength according to the first aspect or the second aspect, it is preferable that the length of the single mode fiber is adjusted such that a difference between the logarithmic value (common logarithm) of the length of the single mode fiber and the logarithmic value (common logarithm) of the length of the measurement target fiber is 0.5 or more at the time of measuring the power of transmission light transmitted through the single mode fiber used as the reference fiber.

According to the method of measuring a cut-off wavelength as the third aspect, the length of the reference fiber is adjusted such that a difference between the logarithmic value of the length of the reference fiber and the logarithmic value of the length of the measurement target fiber is equal to or more than 0.5.

Accordingly, even in a case where there is a large error between the predicted cut-off wavelength and the actual cut-off wavelength of a single mode fiber or a low-bending loss fiber, which is generally used for communication, to be measured, a unique advantage of the present invention can be acquired.

More specifically, a condition that the length of the reference fiber at the time of measuring the power of transmission light transmitted through the reference fiber is adjusted such that the reference fiber propagates only light of the base mode at the predicted cut-off wavelength of the measurement target fiber, can be reliably satisfied.

In addition, a condition that the length of the reference fiber is adjusted such that the cut-off wavelength of the reference fiber is shorter than the predicted cut-off wavelength of the measurement target fiber by at least 10 nm, can be reliably satisfied.

As a result, the accuracy at the time of generating the cut-off wavelength can be further improved.

However, the difference between the lengths at the time of measuring the reference fiber and the measurement target fiber may be 1.3 or more as a difference between the logarithmic values of the lengths of the fibers due to the slope of a steep inclination that can be checked when the wavelength dependence represented as the ratio of the power of transmission light transmitted through the measurement target fiber to the power of transmission light transmitted through the reference fiber, which are actually measured, is represented as a graph.

Since such a difference occurs due to the refractive index profile of the fiber, it can be estimated by acquiring the relationship between the cut-off wavelength of the measurement target fiber and the length of the measurement target fiber based on the refractive index profile of the measurement target fiber.

According to a method of measuring a cut-off wavelength of a fourth aspect of the present invention, in the above-described method of measuring a cut-off wavelength according to any one of the first to third aspects, it is preferable that a fiber formed by a strand drawn by using the same base material as a base material used when the measurement target fiber is measured be used as the reference fiber.

According to such a method of measuring a cut-off wavelength as the fourth aspect, the reference fiber is manufactured from a strand drawn by using the same base material as that used for manufacturing the fiber to be measured by only changing the length.

Accordingly, the reference fiber is manufactured in an easy manner, and the burden for selecting the reference fiber can be omitted.

In addition, in a practical measurement site, the reference fiber can be prepared in an extremely simple manner.

According to a method of measuring a cut-off wavelength of a fifth aspect of the present invention, in the above-described method of measuring a cut-off wavelength according to any one of the first to third aspects, it is preferable that a fiber formed by a strand other than the measurement target fiber be used as the reference fiber.

According to such a method of measuring a cut-off wavelength as the fifth aspect, at a practical measurement site, even in a case where a fiber that is formed by a strand formed by being drawn from the same base material as that used at the time of manufacturing the measurement target fiber is not prepared in advance, the reference fiber can be prepared.

In addition, in a case where another strand is continuously measured, similarly to a conventional method such as a multimode excitation method, by measuring the reference fiber once, measurement can be repeatedly performed.

According to a method of measuring a cut-off wavelength of a sixth aspect of the present invention, in the above-described method of measuring a cut-off wavelength according to any one of the first to fifth aspects, it is preferable that the calculating of the cut-off wavelength of the measurement target fiber based on the wavelength dependence include: acquiring a ratio $A(\lambda)$ by using an equation of $A(\lambda)=10\times\log_{10}\{P_{sig}(\lambda)/P_{ref}(\lambda)\}$ in which the power of transmission light transmitted through the measurement target fiber is denoted by $P_{sig}(\lambda)$, and the power of transmission light transmitted through the reference fiber is denoted by $P_{ref}(\lambda)$; acquiring a reference line by linearly approximating a spectrum of a wavelength region in which only light of a specified mode of the measurement target fiber is propagated on the spectrum of the ratio $A(\lambda)$; acquiring a parallel straight line by shifting the reference line by 0.1 dB in a parallel manner; and determining the wavelength corresponding to an intersection of the parallel straight line and the spectrum of the ratio $A(\lambda)$ of the transmission light power as the cut-off wavelength of the measurement target fiber.

According to such a method of measuring a cut-off wavelength as the sixth aspect, the cut-off wavelength of the single mode fiber can be actually calculated.

According to a method of measuring a cut-off wavelength of the present invention, a situation can be avoided in which a deviation occurs in the calculated cut-off wavelength due to inaccuracy at the time of determining a reference line for calculating the cut-off wavelength.

In addition, by appropriately adjusting the length at the time of measuring the power of transmission light transmitted through a single mode fiber used as the reference fiber, at a position close to the cut-off wavelength of the measurement target fiber, a clear difference between the power of transmission light transmitted through the measurement target fiber and the power of transmission light transmitted through the reference fiber can be acquired.

By acquiring a steep change in the transmission light power ratio $A(\lambda)$ acquired as above, a cut-off wavelength can be accurately calculated.

In addition, by adjusting the length of the reference fiber, the cut-off wavelength of the reference fiber is configured to be shorter than the predicted cut-off wavelength of the measurement target fiber.

Accordingly, the fiber cut-off wavelength or the cable cut-off wavelength of the reference fiber, which are determined by the standard, does not need to be shorter than the cut-off wavelength of the measurement target fiber.

In addition, the reference fiber configured such that the fiber cut-off wavelength or the cable cut-off wavelength, which are determined by the standard, is equal to the cut-off wavelength of the measurement target fiber can be appropriately used.

Furthermore, a reference fiber configured such that the fiber cut-off wavelength or the cable cut-off wavelength, which are determined by the standard, is longer than the cut-off wavelength of the measurement target fiber or a reference fiber configured such that the fiber cut-off wavelength or the cable cut-off wavelength is shorter than the cut-off wavelength of the measurement target fiber can be appropriately used.

In addition, a fiber that is formed from a material different from that of the measurement target fiber or has a configuration different from that of the measurement target fiber can be used.

As a result, the degree of freedom for selecting a reference fiber is markedly higher than that of a conventional method, and accordingly, even at a practical measurement site, the cut-off wavelength can be measured in a simple and easy manner by using an appropriate fiber prepared in advance as the reference fiber.

DESCRIPTION OF THE PREFERRED EMBODIMENTS

Hereinafter, embodiments of the present invention will be described in detail with reference to FIGS. 2 to 10.

Figure 1:
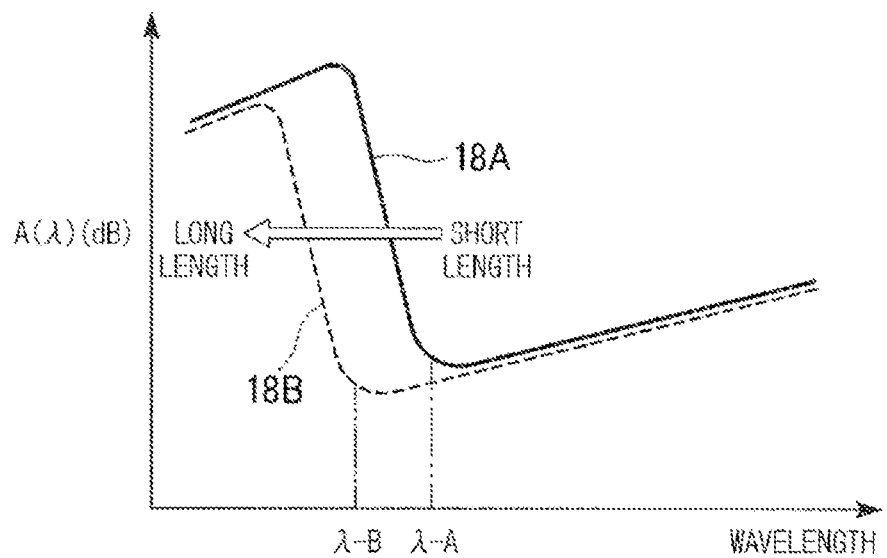
FIG. 1 is a diagram illustrating the premise of a measurement method according to the present invention and is a graph schematically illustrating the dependence of the cut-off wavelength of a single mode fiber on the length.
Figure 2:
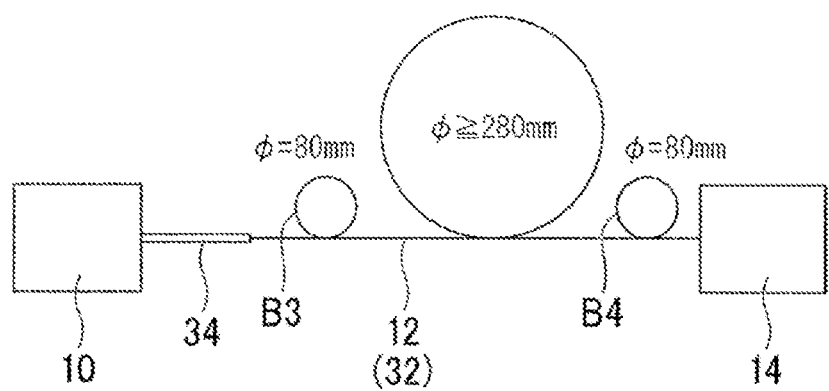
FIG. 2 is a schematic configuration diagram illustrating the configuration of a measurement system used when a cable cut-off wavelength is measured according to a measurement method of the present invention.

FIG. 2 illustrates the configuration of a measurement system used for measuring the power of transmission light transmitted through a reference fiber and the power of transmission light transmitted through a measurement target fiber when a method of measuring a cut-off wavelength according to an embodiment of the present invention is performed.

In FIG. 2, a case where the power $P_{ref}(\lambda)$ of transmission light transmitted through the reference fiber 32 is measured and a case where the power $P_{sig}(\lambda)$ of transmission light transmitted through the measurement target fiber 12 is measured are illustrated in the same drawing.

In FIG. 2, light emitted from a light source unit 10 that is configured of a white light source, a spectroscope, and the like passes through an excitation fiber 34 that is configured of a multi-mode fiber and is guided to the reference fiber 32 or the measurement target fiber 12.

The light transmitted through the reference fiber 32 or the measurement target fiber 12 is received by a light receiving unit 14, and the transmission light power of the reference fiber 32 or the measurement target fiber 12 is measured.

Here, regarding the light source unit 10 and the light receiving unit 14, the configuration of the light source unit 10 and the light receiving unit 14 is not particularly limited as long as they can measure the dependence of an optical fiber on the loss wavelength, and accordingly, the dependence of the power of transmission light on the wavelength.

Thus, the light source unit 10 and the light receiving unit 14 may be the same as a light source unit and a light receiving unit (device, equipment) used in a conventional method of measuring a cut-off wavelength. In addition, in the example illustrated in FIG. 2, bending portions B3 and B4 of 80 mmφ are added to any one of the reference fiber 32 and the measurement target fiber 12.

The reason for this is that, as is paraphrased next, in a case where the cable cut-off wavelength of the measurement target fiber 12 is measured, it is defined in the standard that one circulation of a bending portion of 80 mmφ is disposed at each of both ends of the measurement target fiber by using a commonly used conventional method of measuring a cut-off wavelength such as a multi-mode excitation method.

In a case where the fiber cut-off wavelength of the measurement target fiber 12 is measured, it is defined in the standard that such bending portions B3 and B4 are not disposed.

In FIG. 2, although it is illustrated that the bending portion of 80 mmφ is disposed on both the measurement target fiber 12 and the reference fiber 32, the $_{bending}$ portion of 80 mmφ on the reference fiber 32 may not be necessarily disposed.

In addition, in the example illustrated in FIG. 2, a multi-mode fiber is disposed as the excitation fiber 34 between the light source unit 10 and the reference fiber 32 or the light source unit 10 and the measurement target fiber 12.

A configuration for generating an excitation is not limited to the multi-mode fiber, but, for example, a known configuration used in the excitation of a single mode fiber such as a light collecting lens may be arbitrarily applied.

The measurement target fiber 12 (measurement target) of which the cut-off wavelength is measured is a single mode fiber of a silica type and has a predetermined length.

Here, in a commonly used conventional method of measuring a cut-off wavelength such as a multi-mode excitation method, it is defined in the standard that the length of a sample is 2 m in a case where the fiber cut-off wavelength is measured, and the length of a sample is 22 m in a case where the cable cut-off wavelength is measured.

Thus, in a case where the cut-off wavelength is measured in accordance with the present invention, it is preferable that the length of the measurement target fiber 12 is set to 2 m or 22 m.

Meanwhile, in the method of measuring a cut-off wavelength according to the embodiment of the present invention, a single mode fiber that is configured of a strand drawn by using a base material that is the same as the base material used for manufacturing the measurement target fiber 12 is used as the reference fiber 32.

In other words, the reference fiber 32 is formed by using the same material as that of the measurement target fiber, the properties of the reference fiber 32 such as a refractive index profile and the like are the same as those of the measurement target fiber, and the configuration of the reference fiber 32 is the same as the configuration of the measurement target fiber.

In addition, a single mode fiber that is configured of a strand drawn by using a base material that is different from the base material used for manufacturing the measurement target fiber 12 may be used as the reference fiber 32.

In other words, the reference fiber 32 is formed by using a material that is different from that of the measurement target fiber, the properties of the reference fiber 32 such as a refractive index profile and the like are different from those of the measurement target fiber, and the configuration of the reference fiber 32 is different from the configuration of the measurement target fiber.

A case where a single mode fiber formed from a strand different from the strand configuring the measurement target fiber 1 is used will be described with modifications later.

Here, in order to avoid a complicated description, a case will be described in which the single mode fiber formed by a strand drawn by using the same base material as that used for manufacturing the measurement target fiber 12.

As the reference fiber 32, a reference fiber that is sufficiently longer than the length of the measurement target fiber 12 is prepared.

Here, the sufficiently long reference fiber represents not only the reference fiber being longer than the length of the measurement target fiber 12 in an absolute sense but also the reference fiber 32 having a length for propagating only light of the base mode at the cut-off wavelength of the measurement target fiber 12.

In other words, as described above, in the single mode fiber, the cut-off wavelength is shortened as the length of the single mode fiber is increased.

The length of the reference fiber 32 is adjusted such that the reference fiber 32 has a length for propagating only light of the base mode at the cut-off wavelength of the measurement target fiber 12.

By adjusting the length of the reference fiber 32 as above, a clear difference between the power of transmission light transmitted through the measurement target fiber 12 and the power of transmission light transmitted through the reference fiber 32 can be acquired at a position close to the cut-off wavelength of the measurement target fiber 12.

Thus, in the embodiment of the present invention, instead of simply configuring the length of the single mode fiber at the time of measuring the power of transmission light transmitted through the single mode fiber used as the reference fiber to be longer than the length of the measurement target fiber, the cut-off wavelength of the measurement target fiber 12 is predicted in advance (the cut-off wavelength that is predicted is referred to as a "predicted cut-off wavelength" in the description presented here), and the length of the single mode fiber is adjusted such that the reference fiber propagates only light of the base mode at the predicted cut-off wavelength of the measurement target fiber based on the relationship between the length of the fiber and the cut-off wavelength.

Here, the predicted cut-off wavelength of the measurement target fiber 12 represents a cut-off wavelength that is predicted through experiences or calculations based on the properties of the raw material of the measurement target fiber 12, the configuration of the measurement target fiber 12, or the like.

However, in the actual manufacture of an optical fiber, the occurrence of a deviation in the actual cut-off wavelength due to a variation in the manufacturing conditions, the diameter of a fiber, a variation in the film thickness of a layer configuring the fiber, or the like to some degree is unavoidable.

Thus, in order to determine the predicted cut-off wavelength practically, it is preferable that the relationship between the length of the fiber and the cut-off wavelength is estimated in advance based on the refractive index profile thereof or the like.

In addition, it is preferable that the length of the reference fiber 32 is adjusted such that the cut-off wavelength of the reference fiber is shorter than the predicted cut-off wavelength of the measurement target fiber 12 by at least 10 nm.

In other words, based on the experiments of the inventors of the present invention and others, it was understood that an advantage can be acquired when the cut-off wavelength of the single mode fiber used as the measurement target fiber and the cut-off wavelength of the single mode fiber used as the reference fiber are separated from each other by 10 nm or more.

More specifically, in such a case, at a position close to the cut-off wavelength of the measurement target fiber and the cut-off wavelength of the reference fiber, a clear difference occurs between the power levels of transmission light transmitted through two single mode fibers (the measurement target fiber and the reference fiber).

Accordingly, in the wavelength dependence represented as the ratio between transmission power levels, a steep start clearly appears, and the cut-off wavelength of the measurement target fiber can be acquired more reliably in an easy manner.

Here, it is preferable that the specific length of the reference fiber 32 be determined such that a difference between the logarithmic value (common logarithm) of the length of the reference fiber 32 and the logarithmic value (common logarithm) of the length of the measurement target fiber 12 is at least 0.5.

Even in a case where there is a large error between the predicted cut-off wavelength and the actual cut-off wavelength of a single mode fiber or a low-bending loss fiber, which is generally used for communication, to be measured, a condition that the length of the reference fiber is adjusted, can be reliably satisfied when the difference between the logarithmic value of the length of the reference fiber 32 and the logarithmic value of the length of the measurement target fiber 12 is equal to or more than 0.5 as above.

More specifically, the condition can be reliably satisfied that the length of the reference fiber at the time of measuring the power of transmission light transmitted through the reference fiber is adjusted such that the reference fiber propagates only light of the base mode at the predicted cut-off wavelength of the measurement target fiber.

In addition, the condition that the length of the reference fiber is adjusted such that the cut-off wavelength of the reference fiber is shorter than the predicted cut-off wavelength of the measurement target fiber by 10 nm or more, can be reliably satisfied.

The actual sequence of measuring the cut-off wavelength of the measurement target fiber 12 by adjusting the length of the reference fiber 32 as above will now be described.

First, as a first step, the predicted cut-off wavelength of the measurement target fiber 12 is determined in view of the relationship between the length of the fiber and the cut-off wavelength.

As described above, this may be estimated based on the raw material of the fiber, the configuration of the fiber, the manufacturing method, and the like, and it is preferable that the predicted cut-off wavelength be determined in consideration of a variation in the manufacturing conditions and the like.

Next, as a second step, the length of the reference fiber is adjusted such that the length of the reference fiber 32 is longer than the length of the measurement target fiber 12, and the reference fiber 32 propagates only light of the base mode at the predicted cut-off wavelength of the measurement target fiber 12.

Here, "adjusting the length" in terms of an actual operation represents an operation of selecting a single mode fiber having a length satisfying the above-described conditions of the length, an operation of cutting a predetermined single mode fiber prepared in advance so as to form a fiber having a length satisfying the above-described conditions of the length, or the like.

In addition, as a third step, the power $P_{ref}(\lambda)$ of transmission light transmitted through the reference fiber 32 and the power $P_{sig}(\lambda)$ of transmission light transmitted through the measurement target fiber 12 are measured by using the measurement system as illustrated in FIG. 2.

Thereafter, as a fourth step, the ratio $A(\lambda)$ between the power $P_{ref}(\lambda)$ of transmission light transmitted through the reference fiber 32 and the power $P_{sig}(\lambda)$ of transmission light transmitted through the measurement target fiber 12 is calculated by using the above-described equation.

Figure 3:
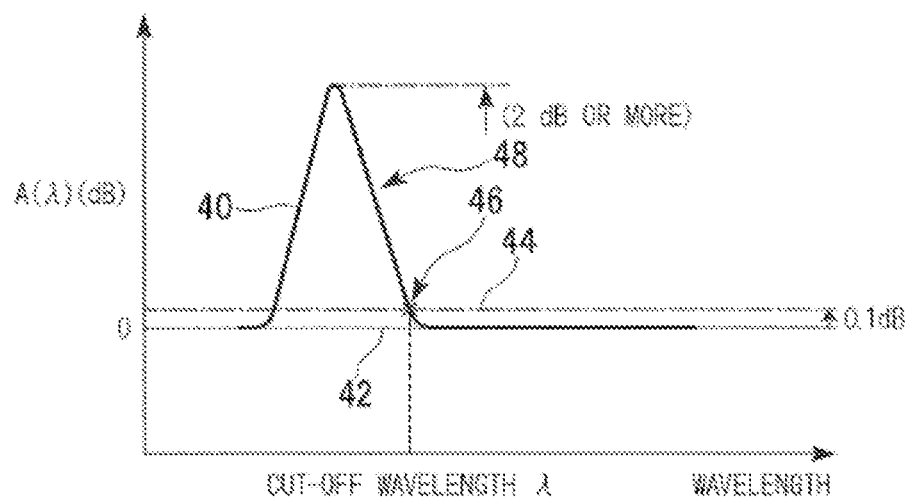
FIG. 3 is a graph that schematically illustrates the wavelength dependence of the ratio $A(\lambda)$ of the power of transmission light transmitted through a measurement target fiber to the power of transmission light transmitted through a reference fiber in the measurement method according to the present invention.

The transmission light power ratio $A(\lambda)$ is schematically illustrated in FIG. 3 while the wavelength is represented in the horizontal axis.

In FIG. 3, a thick solid line 40 represents the wavelength dependence of the ratio $A(\lambda)$.

Here, the value of the transmission light power ratio $A(\lambda)$, at a position close to the cut-off wavelength of the measurement target fiber 12 and the cut-off wavelength of the reference fiber 32, increases steeply from the long wavelength side toward the short wavelength side and furthermore decreases steeply toward the short wavelength side, whereby a peak as denoted by a reference numeral 48 in FIG. 3 appears.

In addition, as a fifth step, the cut-off wavelength $\lambda$ of the measurement target fiber is acquired based on the wavelength dependence of the transmission light power ratio $A(\lambda)$ illustrated in FIG. 3.

Similarly to the multi-mode excitation method and the single mode fiber reference method described above, a straight line acquired by linearly approximating the spectrum of the single mode propagation region of the measurement target fiber 12, that is, the region in which only light of the base mode is propagated is defined as a reference line 42 (a thin solid line shown in FIG. 3).

Next, a wavelength corresponding to the intersection 46 of a straight line 44 (a dashed-dotted line shown in FIG. 3) acquired by shifting the reference line 42 by 0.1 dB in a parallel manner and the spectrum line of the transmission light power ratio $A(\lambda)$ is determined as the cut-off wavelength $\lambda$ of the measurement target fiber 12.

In addition, in the above-described first to fifth steps, generally, in order to measure the cut-off wavelength, it is required that the measurement target fiber be sufficiently excited during measurement of the measurement target fiber.

Thus, in the measurement system shown in FIG. 2, a multi-mode fiber is arranged as the excitation fiber 34 between the light source unit 10 and the measurement target fiber 12 so as to be connected to the light source unit 10 and the measurement target fiber 12.

Here, the configuration for excitation, as described above, is not limited to the connection of the multi-mode fiber, and any other configuration may be employed as long as it can perform sufficient excitation.

Here, in a conventional bending method or a multi-mode excitation method, as an index indicating that the measurement target fiber is sufficiently excited, it is required that the peak of the spectrum of the ratio A(λ) of the power of transmission light transmitted through the measurement target fiber be 2 dB or more.

Also in the present invention, it is preferable that the peak 48 illustrated in FIG. 3 is 2 dB or more.

However, according to the method of the present invention, in a case where the cut-off wavelength of the measurement target fiber and the cut-off wavelength of the reference fiber are close to each other, even when sufficient excitation occurs, a peak (a peak of 2 dB or more) having a sufficient height may not appear in the spectrum of the transmission light power ratio A(λ).

In such a case, it is preferable that a checking test of the excitation state is performed.

In other words, first, according to the commonly used conventional multi-mode excitation method, the transmission light power is measured for each one of a measurement target sample and a reference fiber (long fiber) according to the method of the present invention.

In a case where a peak of 2 dB or more appears in the transmission light power ratio A(λ) according to the multi-mode excitation method, even when a peak of 2 dB or more does not appear in the method of the present invention, sufficient excitation can be assumed.

In addition, the fiber used as the reference fiber at the time of measuring the cut-off wavelength of the measurement target fiber according to the method of the present invention may be a single mode fiber.

Furthermore, the fiber used as the reference fiber as above is not limited to a fiber that is formed from a strand drawn from the same base material as the base material used for manufacturing the measurement target fiber.

In other words, a single mode fiber configured of a strand other than the measurement target fiber (the raw material or the fiber configuration of the reference fiber is different from that of the measurement target fiber) may be used as the reference fiber.

In such a case, the fiber is not limited to a fiber of which the cut-off wavelength at a standard length (2 m or 22 m) of the reference fiber is equal to the cut-off wavelength of the measurement target fiber.

A fiber of which the cut-off wavelength at the standard length is longer than the cut-off wavelength of the measurement target fiber or a fiber of which the cut-off wavelength at the standard length is shorter than the cut-off wavelength of the measurement target fiber can be used as the reference fiber.

For example, even in a case in which the cut-off wavelength of the fiber at the standard length is longer than the predicted cut-off wavelength of the measurement target fiber, by satisfying the condition of the length as described above by adjusting the length of the fiber to be sufficiently longer than that of the measurement target fiber, the cut-off wavelength of the measurement target fiber can be measured according to the method of the present invention.

In addition, the method of the present invention, unlike the bending method, can be applied to a low-bending loss optical fiber.

Furthermore, the method of the present invention is not limited to the low-bending loss optical fiber but can be applied to a general single mode fiber used for communication as well.

Next, experimental examples performed as the premise of the present invention and experimental examples performed for verifying the effect of the present invention will be described with reference to FIGS. 4 to 10.

However, the description of experimental examples presented below is not for the purpose of limiting the technical scope of the present invention.

EXPERIMENTAL EXAMPLE 1

Figure 4:
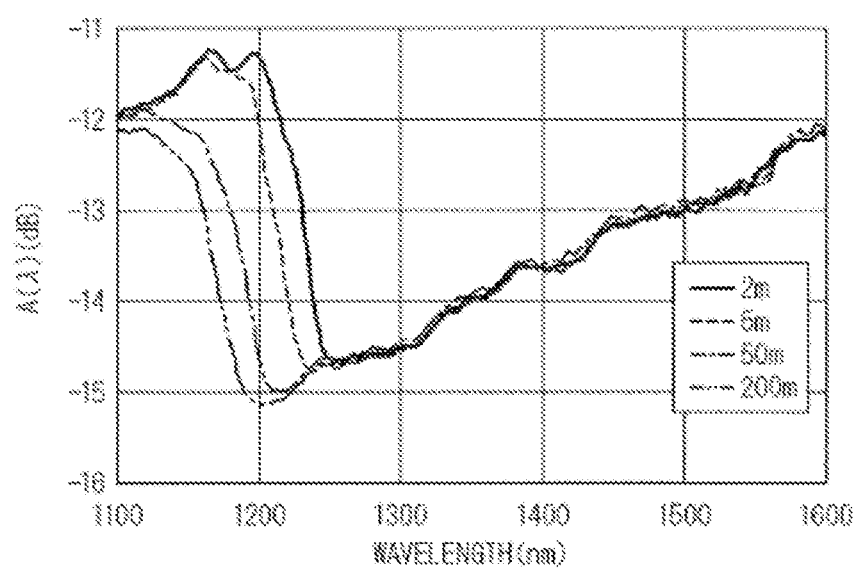
FIG. 4 is a graph illustrating the results of measurement of the dependence of the cut-off wavelength of the single mode fiber on the length according to a multi-mode excitation method in Experimental Example 1.

The results of a test are illustrated in FIG. 4 showing that the cut-off wavelength of the single mode fiber acquired by measurement changes in accordance with the length of a fiber used in the measurement, in other words, the cut-off wavelength is shortened as the length of the fiber is increased is illustrated in FIG. 4.

In this experiment, a general single mode fiber used for communication was used as the measurement target fiber, and the power $P_{sig}(λ)$ of transmission light transmitted through the measurement target fiber that was formed by a single mode fiber of various kinds of lengths (2 m to 200) and the power $P_{ref}(λ)$ of transmission light transmitted through the reference fiber having a constant length were measured according to the multi-mode excitation method.

The wavelength dependency of the ratio A(λ) on the length of the fiber when the ratio A(λ) of the transmission light power $P_{sig}(λ)$ to the transmission light power $P_{ref}(λ)$ was measured is illustrated in FIG. 4.

In FIG. 4, a portion at which the ratio A(λ) rises steeply in the range of about 1250 nm to 1150 nm from the long wavelength side toward the short wavelength side corresponds to a cut-off wavelength.

It can be understood that the cut-off wavelength is shortened as the length of the fiber is increased.

Based on this result, it is apparent that a single mode fiber that is sufficiently longer than the measurement target fiber can be used as a reference fiber of which the cut-off wavelength is shorter than that of the measurement target fiber.

Figure 5:
FIG. 5 is a graph acquired by extracting an example in which the length is 2 m from the results illustrated in FIG. 4 according to Experimental Example 1.

In addition, here, data only for a length of the measurement target fiber of 2 m is extracted from FIG. 4 and is illustrated in FIG. 5.

While this is a part of the measurement result according to a conventional multi-mode excitation method, in a case where measurement is performed according to the multi-mode excitation method, it is apparent from FIG. 5 that a wave occurs in a long wavelength-side portion of the wavelength dependency of the transmission light power ratio A(λ) that is to be linearly approximate.

Accordingly, in this case, the reference line differs depending on the way in which linearly approximate regions are accounted for or the method or calculation used to do so, and accordingly, it is understood that a deviation will occur in the calculation result of the cut-off wavelength.

In addition, more specifically, the single mode fiber used as the measurement target fiber in this Experimental Example 1 is a single mode fiber that is in compliance with ITU-T G.652.D.

EXPERIMENTAL EXAMPLE 2

In Experimental Example 2, a measurement target fiber, which has a length of 2 m, configured of a single mode fiber formed by a strand drawn by using the same base material as the base material used for manufacturing the fiber used in Experimental Example 1 will be described.

In addition, a fiber, which has a length of 200 m, formed by a strand drawn by using the same base material as the base material used for manufacturing the measurement target fiber was used as the reference fiber.

Next, the power $P_{sig}(\lambda)$ of transmission light transmitted through the measurement target fiber and the power $P_{ref}(\lambda)$ of transmission light transmitted through the reference fiber were measured by using the method of the present invention, and the ratio $A(\lambda)$ of the transmission light power $P_{sig}(\lambda)$ to the transmission light power $P_{ref}(\lambda)$ was measured.

Figure 6:
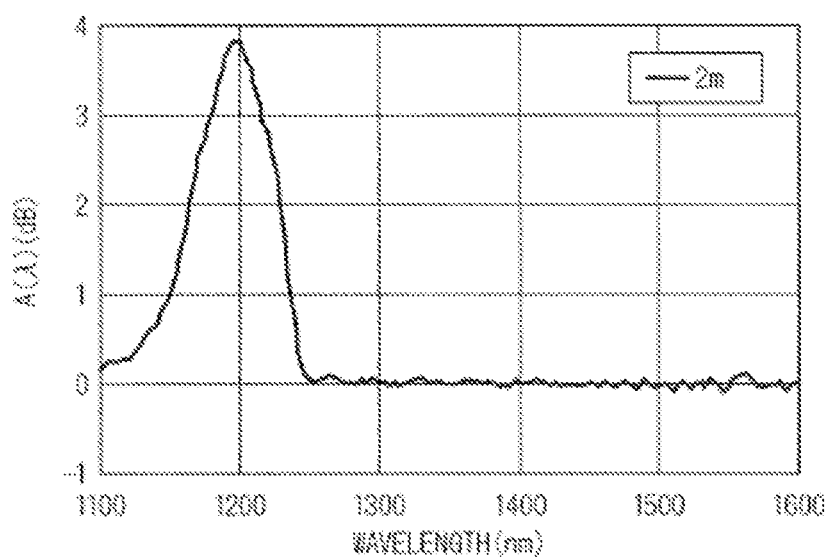
FIG. 6 is a graph that illustrates the results of measurement of the wavelength dependency of the ratio $A(\lambda)$ of the power of transmission light transmitted through a measurement target fiber to the power of transmission light transmitted through a reference fiber using the method according to the present invention in Experimental Example 2.

The wavelength dependency of the transmission light power ratio $A(\lambda)$ at this time is illustrated in FIG. 6.

In this case, as is apparent from FIG. 6, a wave occurring in the case of the multi-mode excitation method illustrated in FIG. 5 did not occur in a long wavelength-side portion (the single mode propagation region of the measurement target fiber) of the wavelength dependence of the transmission light power ratio $A(\lambda)$ which is to be linearly approximated.

Accordingly, it is difficult for an error of the linear approximation to occur, and it is apparent that the reference line can be reliably determined in an easy manner.

In addition, in Experimental Example 2, as a predicted cut-off wavelength of the measurement target fiber, about 1250 nm was assumed.

Here, in a reference fiber, which has a length of 200 m, formed by a strand drawn by using the same base material as the base material used for manufacturing the measurement target fiber having a length of 2 m, the cut-off wavelength of the reference fiber is estimated to be about 1200 nm.

Accordingly, a length of the reference fiber at the time of measuring transmission light power transmitted through the reference fiber satisfies the above-described condition that the length of the single mode fiber be adjusted such that the reference fiber propagates only light of the base mode at the predicted cut-off wavelength of the measurement target fiber.

In addition, it is apparent that the condition that the length of the reference fiber is adjusted such that the cut-off wavelength of the reference fiber is shorter than the predicted cut-off wavelength of the measurement target fiber by 10 nm or mode, is satisfied.

Furthermore, the cut-off wavelength of the measurement target fiber that is finally calculated through Experimental Example 2 was 1242.7 nm.

EXPERIMENTAL EXAMPLE 3

In Experimental Example 3, a measurement target fiber, which has a length of 22 m, configured of a single mode fiber formed by a low-bending loss fiber will be described.

In addition, as the reference fiber, a fiber, which has a length of 200 m, formed by a strand drawn by using the same base material as the base material used for manufacturing the measurement target fiber is used.

Next, the power $P_{sig}(\lambda)$ of transmission light transmitted through the measurement target fiber and the power $P_{ref}(\lambda)$ of transmission light transmitted through the reference fiber were measured by using the method of the present invention, and the ratio $A(\lambda)$ of the transmission light power $P_{sig}(\lambda)$ to the transmission light power $P_{ref}(\lambda)$ was measured.

Figure 7:
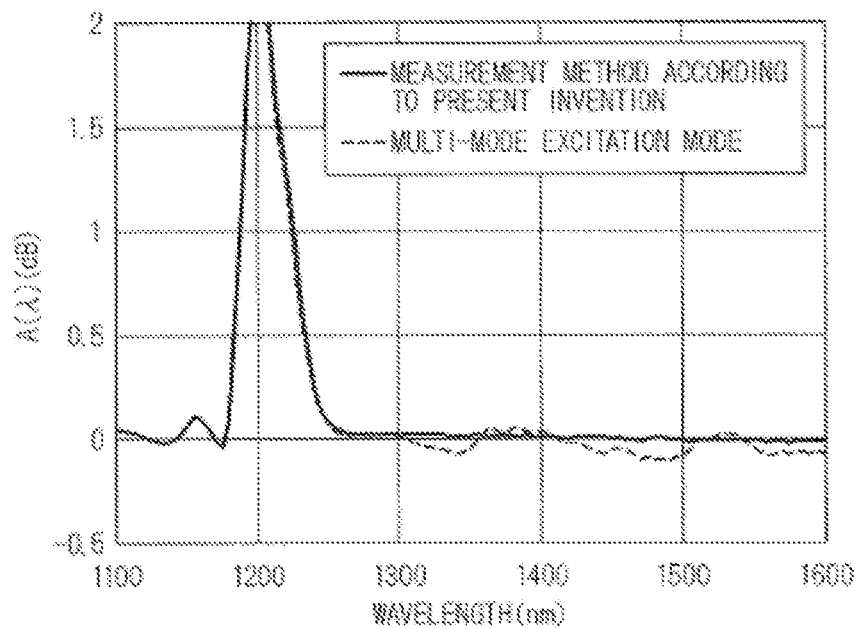
FIG. 7 is a graph that illustrates results of measurement of the wavelength dependency of the ratio $A(\lambda)$ of the power of transmission light transmitted through a measurement target fiber to the power of transmission light transmitted through a reference fiber using the method according to the present invention and a multi-mode excitation method in Experimental Example 3.

The wavelength dependency of the transmission light power ratio $A(\lambda)$ at this time is denoted by a solid line illustrated in FIG. 7.

In addition, in Experimental Example 3, as a predicted cut-off wavelength of the measurement target fiber, although about 1250 nm was assumed, in the reference fiber, which has a length of 200 m, configured of the same raw material as that of the measurement target fiber having a length of 22 m, the cut-off wavelength is estimated to be about 1200 nm.

Accordingly, a length of the reference fiber at the time of measuring transmission light power transmitted through the reference fiber satisfied the above-described condition that the length of the single mode fiber is adjusted such that the reference fiber propagates only light of the base mode at the predicted cut-off wavelength of the measurement target fiber.

In addition, it is apparent that the condition is satisfied that the length of the reference fiber is adjusted such that the cut-off wavelength of the reference fiber is shorter than the predicted cut-off wavelength of the measurement target fiber by 10 nm or mode.

In addition, more specifically, the measurement target fiber used in this Experimental Example 3 is configured of a single mode fiber that is in compliance with ITU-T G.657.A.2.

In addition, for a comparison with the above-described experiment, a measurement target fiber, which has a length of 22 m, formed by a low-bending loss fiber as above will be described.

A multi-mode fiber was used as the reference fiber, and the power $P_{sig}(\lambda)$ of transmission light transmitted through the measurement target fiber and the power $P_{ref}(\lambda)$ of transmission light transmitted through the reference fiber were measured according to a conventional multi-mode excitation method, and the ratio $A(\lambda)$ of the transmission light power $P_{sig}(\lambda)$ to the transmission light power $P_{ref}(\lambda)$ was measured.

The wavelength dependency of the transmission light power ratio $A(\lambda)$ at this time is converted such that the reference line is a zero base for determining the cut-off wavelength and is denoted by a broken line in FIG. 7.

As is apparent from FIG. 7, while a wave occurs in a long-wavelength side region in a case (broken line) where the conventional multi-mode excitation method is used, a wave does not substantially occur in a case (solid line) where the method of the present invention is used.

Regarding the cut-off wavelength calculated in this Experimental Example 3, the cut-off wavelength according to the method of the present invention was 1249.1 mm, the cut-off wavelength according to the conventional multi-mode excitation method was 1249.0 nm, and there was no large difference between the two cut-off wavelengths.

It is thought that the reason for this is that the linear approximation, which is performed for determining the reference line, according to the conventional multi-mode excitation method was accidently appropriate.

EXPERIMENTAL EXAMPLE 4

In Experimental Example 4, a measurement target fiber having a length of 22 m was cut out from a low-bending loss fiber of the same type as the low-bending loss fiber used in Experimental Example 3.

As the reference fiber, a fiber that is the same as the reference fiber used in the method of the present invention in Experimental Example 3 was used.

According to the method of the present invention, the power $P_{sig}(\lambda)$ of transmission light transmitted through the measurement target fiber was measured.

In addition, as data of the power $P_{ref}(\lambda)$ transmitted through the reference fiber, data according to the method of the present invention, which was used in Experimental Example 3, was used without any change.

The ratio $A(\lambda)$ of the transmission light power $P_{sig}(\lambda)$ to the transmission light power $P_{ref}(\lambda)$ was measured.

Figure 8:
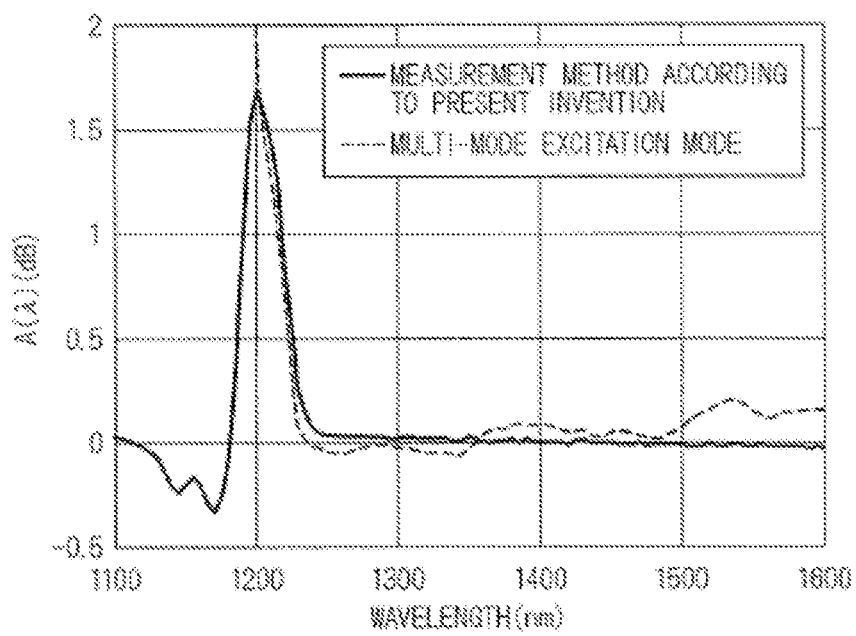
FIG. 8 is a graph that illustrates results of measurement of the wavelength dependency of the ratio $A(\lambda)$ of the power of transmission light transmitted through a measurement target fiber to the power of transmission light transmitted through a reference fiber using the method according to the present invention and a multi-mode excitation method in Experimental Example 4.

The wavelength dependence of the transmission light power ratio $A(\lambda)$ is denoted by a solid line in FIG. 8.

In addition, also in Experimental Example 4, similarly to the method of the present invention described in Experimental Example 3, the predicted cut-off wavelength of the measurement target fiber was assumed to be about 1230 nm.

In addition, for a comparison with the above-described experiment, a measurement target fiber, which has a length of 22 m, formed by a low-bending loss fiber as above will be described.

A multi-mode fiber was used as the reference fiber, and the power $P_{sig}(\lambda)$ of transmission light transmitted through the measurement target fiber was measured according to the conventional multi-mode excitation method.

In addition, as data of the power $P_{ref}(\lambda)$ of transmission light transmitted through the reference fiber, the data according to the multi-mode excitation method in Experimental Example 3 was used without any change, and the ratio $A(\lambda)$ of the transmission light power $P_{sig}(\lambda)$ to the transmission light power $P_{ref}(\lambda)$ was measured.

The graph of the wavelength dependency of the transmission light power ratio $A(\lambda)$ at this time is converted such that the reference line is a zero base for determining the cut-off wavelength and is denoted by a broken line in FIG. 8.

Regarding the cut-off wavelength calculated in this Experimental Example 4, the cut-off wavelength according to the method of the present invention was 1238.7 nm, the cut-off wavelength according to the conventional multi-mode excitation method was 1229.7 nm, and, differently from Experimental Example 3, there was a considerable difference between the two cut-off wavelengths.

Figure 9:
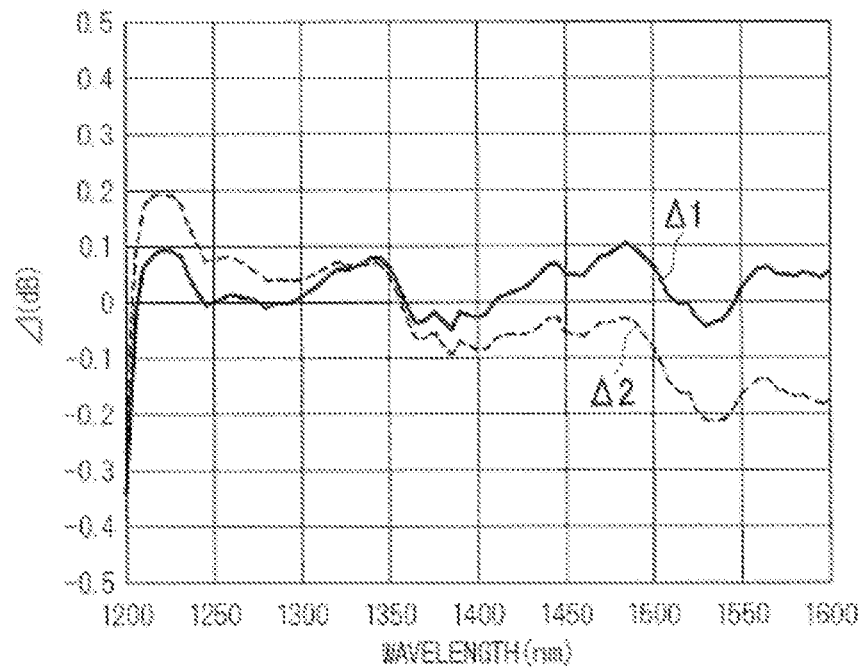
FIG. 9 is a graph illustrating the wavelength dependency of a difference $\Delta 1$ between the transmission light power ratio $A(\lambda)$ acquired according to the method of the present invention and the transmission light power ratio acquired according to the multi-mode excitation method in Experimental Example 3 (FIG. 7) and a difference $\Delta 2$ between the transmission light power ratio $A(\lambda)$ according to the method of the present invention and the transmission light power ratio $A(\lambda)$ according to the multi-mode excitation method in Experimental Example 4 (FIG. 8).

Here, a difference $\Delta 1$ between the transmission light power ratio $A(\lambda)$ acquired according to the method of the present invention in Experimental Example 3 (FIG. 7) and the transmission light power ratio $A(\lambda)$ acquired according to the conventional multi-mode excitation method is denoted by a solid line in FIG. 9.

In addition, a difference $\Delta 2$ between the transmission light power ratio $A(\lambda)$ acquired according to the method of the present invention in Experimental Example 4 (FIG. 8) and the transmission light power ratio $A(\lambda)$ acquired according to the multi-mode excitation method is denoted by a broken line in FIG. 9.

As can be understood from FIG. 9, in Experimental Example 3 and Experimental Example 4, there are large differences 41 and 42 between the transmission light power ratios acquired according to the method of the present invention and the transmission light power ratios acquired according to the multi-mode excitation method.

In Experimental Example 3 and Experimental Example 4, as data of the transmission light power $P_{ref}(\lambda)$ transmitted through the reference fiber according to the method of the present invention, the same data was used.

In addition, as data of the transmission light power $P_{ref}(\lambda)$ transmitted through the reference fiber in the measurement according to the conventional multi-mode excitation method, the same data was used.

Accordingly, it is understood that a difference between the difference $\Delta 1$ and the difference $\Delta 2$ as described above is an error occurring when the reference line is determined according to the multi-mode excitation method.

In other words, in Experimental Example 3 and Experimental Example 4, the data of the transmission light power $P_{ref}(\lambda)$ transmitted through the reference fiber according to the multi-mode excitation method and the data of the transmission light power $P_{ref}(\lambda)$ transmitted through the reference fiber according to the method of the present invention are common.

However, according to the multi-mode excitation method, in the wavelength dependence of the transmission light power ratio $A(\lambda)$, a large wave is present in the base mode region (a region relating to the determination of a reference line) of the measurement target fiber, and accordingly, a deviation occurs when the reference line is determined through linear approximation.

As a result, it is understood that a deviation occurs also in the calculated cut-off wavelength.

In contrast to this, according to the method of the present invention, since the single mode fiber is used as the reference fiber, the occurrence of such a wave is avoided, and there is a small error in the determination of the reference line, whereby measurement of a more accurate cut-off wavelength can be performed.

EXPERIMENTAL EXAMPLE 5

In Experimental Example 5, a measurement target fiber, which has a length of 22 m, configured of a single mode fiber formed by a strand of the same kind as that of the low-bending loss fiber used in Experimental Example 3 will be described.

As the single mode fiber as the reference fiber, a fiber, which has a length of 100 m, configured of a strand different from the measurement target fiber, in other words, a single mode fiber generally used for communication, and more particularly, a single mode fiber that is in compliance with ITU-T G.652.D was used.

Next, the power $P_{sig}(\lambda)$ of transmission light transmitted through the measurement target fiber and the power $P_{ref}(\lambda)$ of transmission light transmitted through the reference fiber were measured in accordance with the method of the present invention, and the ratio $A(\lambda)$ of the transmission light power $P_{sig}(\lambda)$ to the transmission light power $P_{ref}(\lambda)$ was measured.

Figure 10:
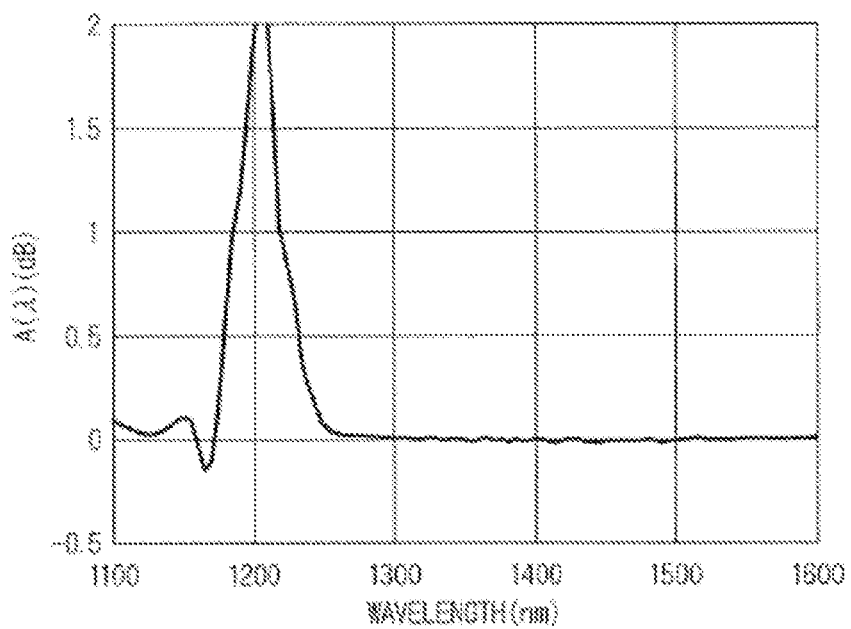
FIG. 10 is a graph that illustrates the results of measurement of the wavelength dependency of the ratio $A(\lambda)$ of the power of transmission light transmitted through a measurement target fiber to the power of transmission light transmitted through a reference fiber using the method according to the present invention in Experimental Example 5.
Figure 11A:
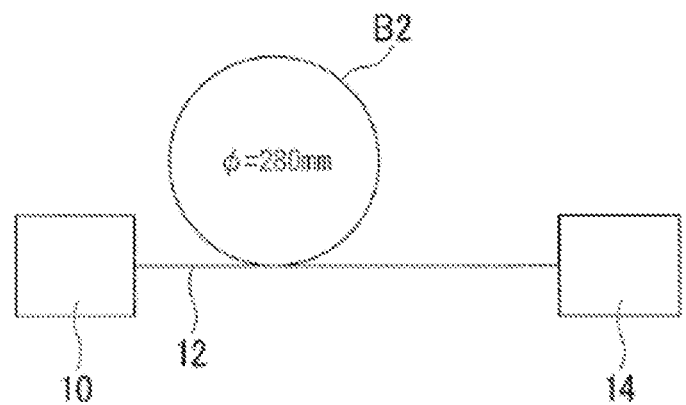
FIG. 11A is a schematic configuration diagram illustrating the configuration of a measurement system used when a cut-off wavelength is measured according to a conventional bending method and illustrates a case where a bending portion is not effectively added to the measurement target fiber.
Figure 11B:
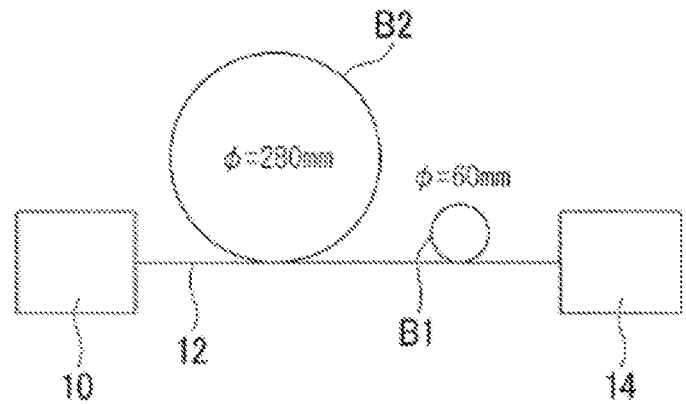
FIG. 11B is a schematic configuration diagram illustrating the configuration of a measurement system used when a cut-off wavelength is measured according to a conventional bending method and illustrates a case where a bending portion is effectively added to the measurement target fiber.
Figure 12A:
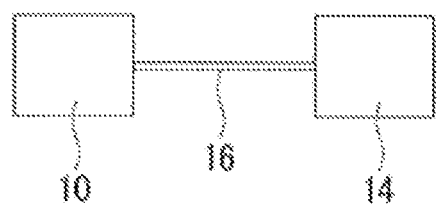
FIG. 12A is a schematic configuration diagram illustrating the configuration of a measurement system used when a cut-off wavelength is measured according to a conventional multi-mode excitation method and illustrates a case where measurement of a reference fiber is performed.
Figure 12B:
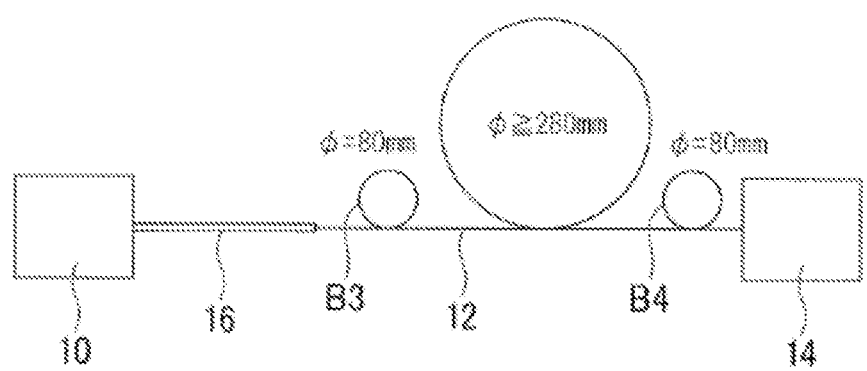
FIG. 12B is a schematic configuration diagram illustrating the configuration of a measurement system used when a cut-off wavelength is measured according to a conventional multi-mode excitation method and illustrates a case where a measurement target fiber is measured.
Figure 13:
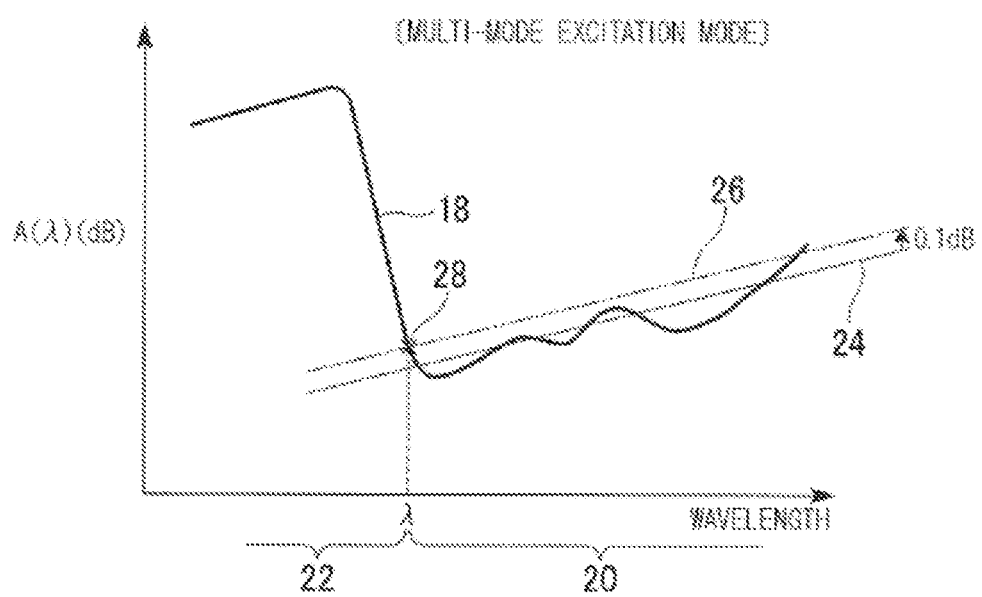
FIG. 13 is a graph that illustrates the wavelength dependence of the ratio $A(\lambda)$ of the power of transmission light transmitted through a measurement target fiber to the power of transmission light transmitted through a reference fiber in a case where a cut-off wavelength is measured according to a conventional multi-mode excitation method.

The wavelength dependency of the transmission light power ratio $A(\lambda)$ at this time is illustrated in FIG. 10.

In addition, in Experimental Example 5, as a predicted cut-off wavelength of the measurement target fiber, although about 1250 nm was assumed, in the reference fiber, which has a length of 100 m, having a refractive index profile different from that of the measurement target fiber having a length of 22 m, the cut-off wavelength is estimated to be about 1200 nm.

Accordingly, a length of the reference fiber at the time of measuring transmission light power transmitted through the reference fiber satisfied the above-described condition that the length of the single mode fiber is adjusted such that the reference fiber propagates only light of the base mode at the predicted cut-off wavelength of the measurement target fiber.

In addition, it is apparent that the condition that the length of the reference fiber is adjusted such that a difference between the logarithmic value (common logarithm) of the length of the reference fiber and the logarithmic value (common logarithm) of the length of the measurement target fiber is at least 0.5, is satisfied.

The cut-off wavelength calculated in Experimental Example 5 was 1248.9 nm.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A method of measuring a cut-off wavelength of a silica-based fiber, the method comprising:
   preparing a single mode fiber as a reference fiber;
   preparing a measurement target fiber;
   estimating, at an estimation unit, a relationship between a length of the measurement target fiber and a cut-off wavelength thereof in advance based on a refractive index profile thereof, thereby predicting a predicted cut-off wavelength;
   adjusting, at an adjustment unit, a length of the reference fiber such that the length of the reference fiber is longer than a length of the measurement target fiber so that the length of the reference fiber is adjusted such that a difference between a logarithmic value, in common logarithm, of the length of the reference fiber and a logarithmic value, in common logarithm, of the length of the measurement target fiber is 0.5 or more at the time of measuring power of transmission light transmitted through the reference fiber and the reference fiber propagates only light of a base mode at the predicted cut-off wavelength of the measurement target fiber;
   measuring, at a measurement unit, wavelength dependence of power of transmission light transmitted through the reference fiber and wavelength dependence of power of transmission light transmitted through the measurement target fiber; and
   calculating, at a calculation unit, a cut-off wavelength of the measurement target fiber based on wavelength dependence that is represented as a ratio of the power of transmission light transmitted through the measurement target fiber to the power of transmission light transmitted through the reference fiber.

2. The method according to claim 1, wherein the length of the reference fiber at the time of measuring the power of the transmission light is adjusted such that the cut-off wavelength of the reference fiber is shorter than the predicted cut-off wavelength of the measurement target fiber by at least 10 nm.

3. The method according to claim 1, wherein a fiber formed by a strand drawn by using the same base material as a base material used when the measurement target fiber is manufactured is used as the reference fiber.

4. The method according to claim 1, wherein a fiber formed by a strand other than the measurement target fiber is used as the reference fiber.

5. The method according to claim 1, wherein
   the calculating of the cut-off wavelength of the measurement target fiber based on the wavelength dependence includes:
   acquiring, at an acquisition unit, a transmission power ratio $A(\lambda)$ by using an equation of $A(\lambda)=10\times\log_{10}\{P_{sig}(\lambda)/P_{ref}(\lambda)\}$ in which the power of transmission light transmitted through the measurement target fiber is denoted by $P_{sig}(\lambda)$, and the power of transmission light transmitted through the reference fiber is denoted by $P_{ref}(\lambda)$;
   acquiring, at an acquisition unit, a reference line by linearly approximating a spectrum of a wavelength region in which only light of a specified mode of the measurement target fiber is propagated on the spectrum of the ratio $A(\lambda)$;
   acquiring, at an acquisition unit, a parallel straight line by shifting the reference line by 0.1 dB in a parallel manner; and
   determining, at a determination unit, a wavelength corresponding to an intersection of the parallel straight line and the spectrum of the ratio $A(\lambda)$ of the transmission light power as the cut-off wavelength of the measurement target fiber.

* * * * *